United States Patent [19]
Chriki

[11] Patent Number: 5,707,981
[45] Date of Patent: Jan. 13, 1998

[54] SYNERGISTIC PHARMACEUTICAL COMPOSITIONS

[75] Inventor: Georges Chriki, Jerusalem, Israel

[73] Assignee: Psorial, L.L.C., New York, N.Y.

[21] Appl. No.: 469,371

[22] Filed: Jun. 6, 1995

Related U.S. Application Data

[63] Continuation-in-part of Ser. No. 281,642, Jul. 28, 1994, abandoned.

[51] Int. Cl.⁶ .......................... A61K 31/56; A61K 31/58
[52] U.S. Cl. ........................................ 514/170; 514/174
[58] Field of Search ................................. 514/170, 174

[56] References Cited

U.S. PATENT DOCUMENTS

| | | | |
|---|---|---|---|
| 2,990,401 | 6/1961 | Bernstein et al. | 540/63 |
| 3,035,050 | 5/1962 | Hydorn | 540/63 |
| 3,892,857 | 7/1975 | Difazio et al. | 514/174 |
| 3,899,581 | 8/1975 | Agusti | 514/174 |
| 3,934,013 | 1/1976 | Poulsen | 514/170 |
| 4,107,161 | 8/1978 | Agusti | 540/70 |
| 4,233,295 | 11/1980 | Hill et al. | 424/238 |

FOREIGN PATENT DOCUMENTS

| | | |
|---|---|---|
| 020117 | 5/1980 | European Pat. Off. |
| 0196121 | 2/1986 | European Pat. Off. |
| 173478 | 3/1986 | European Pat. Off. |
| 2354 | 2/1964 | France . |
| 4119170 | 12/1992 | Germany . |

OTHER PUBLICATIONS

Cutis (United States), Aug. 1984, vol. 34 No. 2 pp. 190–194, Bicker DR "A comparative study of amcinonide and halcinonide in the treatment of eczematous dermatitis".

Cutis, vol. 42, No. 1, 1990, pp. 84–88 The Actiderm Multi–Center Study Group.

The British Journal of Clinical Practice, vol. 20, No. 10, Oct. 1966, David Haler, "An Assessment of Combined Corticosteriods," pp. 511–514.

*Primary Examiner*—Theodore J. Criares
*Attorney, Agent, or Firm*—Hamilton, Brook, Smith & Reynolds, P.C.

[57] ABSTRACT

A pharmaceutical composition comprises a synergistic combination of about 0.01–0.15% by wt. triamcinolone acetonide and about 0.04–0.3% by wt. halcinonide as active ingredients, in combination with a pharmaceutically acceptable carrier.

15 Claims, 10 Drawing Sheets

FIG.8A
FIG.8B
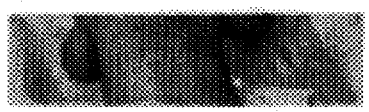
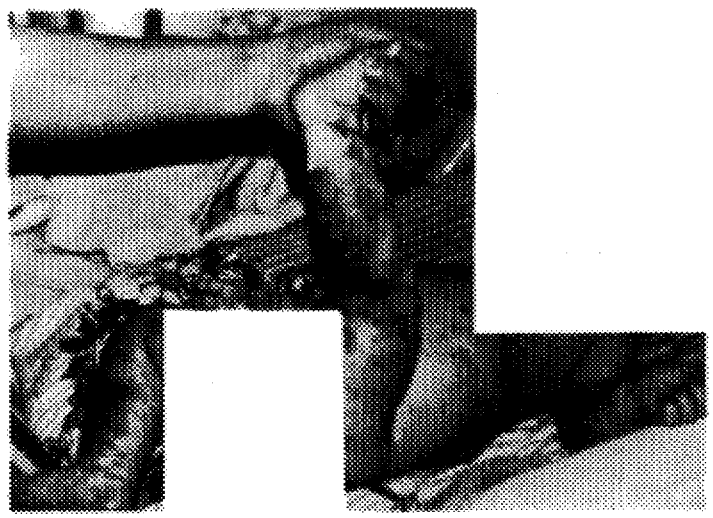
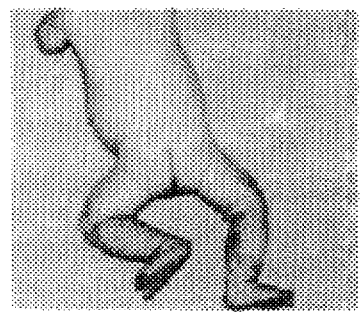
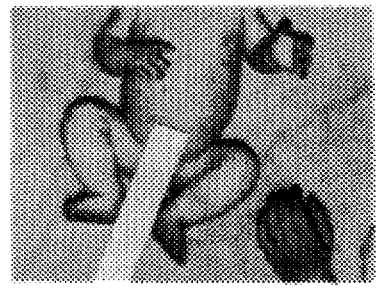
FIG.8C
FIG.8D

SYNERGISTIC PHARMACEUTICAL COMPOSITIONS

This is a continuation-in-part of application Ser. No. 08/281,642 filed in the United States Patent and Trademark Office on or about Jul. 28, 1994, now abandoned.

The present invention relates to a pharmaceutical composition for treating psoriasis. More particularly, the present invention relates to a composition containing 16α, 17α-substituted methylenedioxy steroids as active ingredients therein.

It has been known for over 25 years that 11-substituted 16α,17α-substituted methylene dioxysteroids of the pregnane series, as described, e.g., in U.S. Pat. No. 2,990,401, have high anti-inflammatory activity and can be used topically in the treatment of burns, rheumatoid arthritis, allergies, psoriasis and other skin disorders.

Among the compounds taught in said patent, it is now well-known that triamcinolone acetonide, which is 9α-fluoro-11β-21-dihydroxy-16α,17α-isopropylidenedioxy-1,4-pregnadiene-3,20-dione, has proved particularly useful in the treatment of dermatological conditions. The compound has been proved to have marked efficacy in the treatment of dermatosis, eczema, neurodermitis, impetigo, psoriasis, pruritis and other related diseases.

Similarly, in U.S. Pat. No. 3,892,857 there is described and claimed a steroid formulation having enhanced properties for topical application, comprising 21-chloro-9-fluoro-11-hydroxy-16,17-[(1-methyl-ethylidene)bis(oxy)]pregn-4-ene-3,20-dione in a vehicle containing as major ingredients propylene glycol and water.

The present invention relates to a pharmaceutical composition for treating psoriasis. More particularly, the present invention relates to a composition containing 16α,17α-substituted methylenedioxy steroids as active ingredients therein.

It has been known for over twenty-five years that 11-substituted 16α,17α-substituted methylene dioxysteroids of the pregnane series, as described, e.g., in U.S. Pat. No. 2,990,401, have high anti-inflammatory activity and can be used topically in the treatment of burns, rheumatoid arthritis, allergies, psoriasis and other skin disorders.

Among the compounds taught in said patent it is now well known that triamcinolone acetonide, which is 9α-fluoro-11β21-dihydroxy-16α,17α-isopropylidenedioxy-1,4-pregnadiene-3,20-dione, has proved particularly useful in the treatment of dermatological conditions. The compound has been proved to have marked efficacy in the treatment of dermatosis, eczema, neurodermitis, impetigo, psoriasis, pruritis and other related diseases.

Similarly, in U.S. Pat. No. 3,892,857 there is described and claimed a steroid formulation having enhanced properties for topical application comprising 21-chloro-9-fluoro-11-hydroxy-16,17-[(1-methyl-ethylidene)bis(oxy)]pregn-4-ene-3,20-dione in a vehicle containing as major ingredients propylene glycol aid water.

Said compound has subsequently become known generally as halcinonide and is marketed as a topical anti-inflammatory compound.

While both of said compounds are successfully marketed and are known to ease the suffering caused by psoriasis by stopping the itching, and even cleaning the skin of crust, the basic psoriasis remains uncured.

DESCRIPTION OF DRAWINGS

FIG. 1A through 8D illustrate the synergistic effect of the composition of Examples 1–3.

Figure 1A:
Figure 1B:
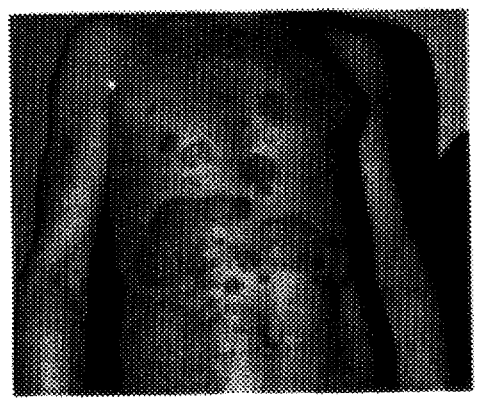
Figure 1C:
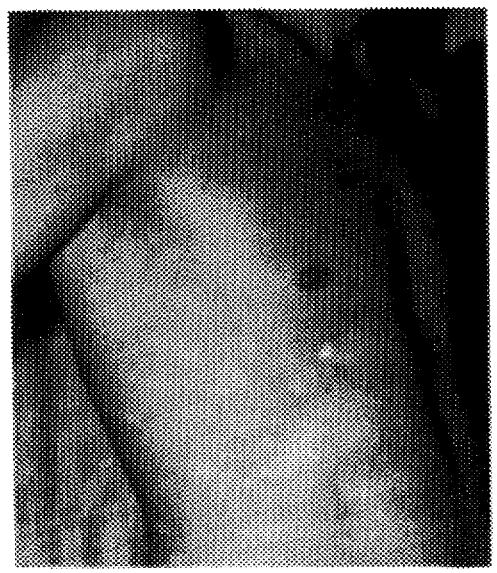
Figure 1D:
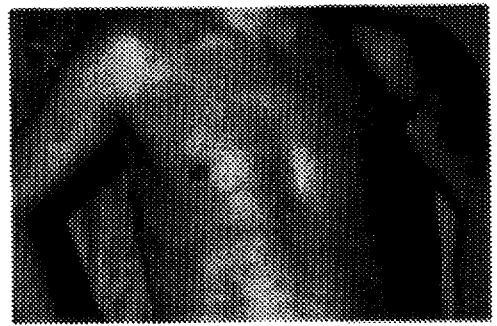
Figure 2A:
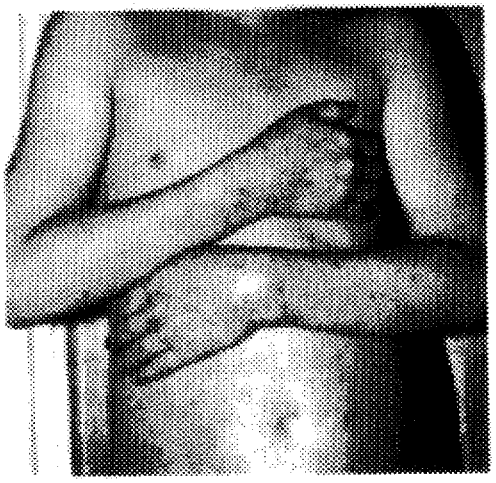
Figure 2B:
Figure 2C:
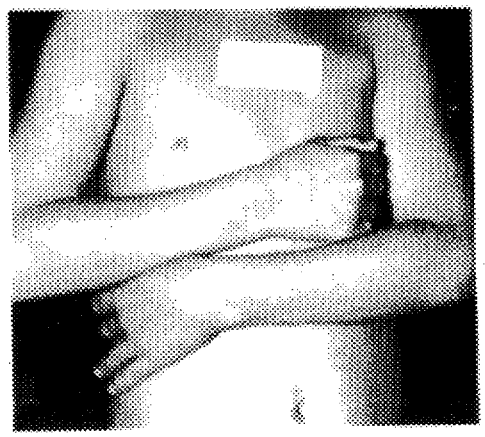
Figure 2D:
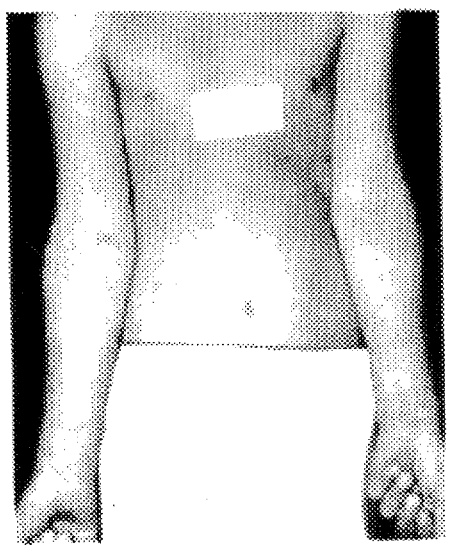
Figure 3A:
Figure 3B:
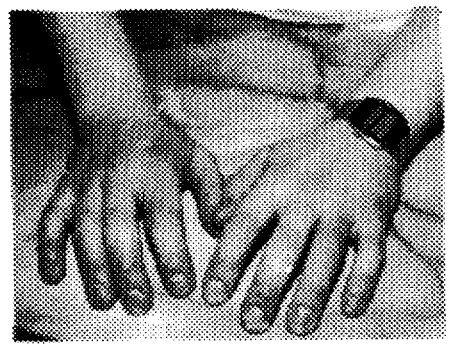
Figure 4A:
Figure 4B:
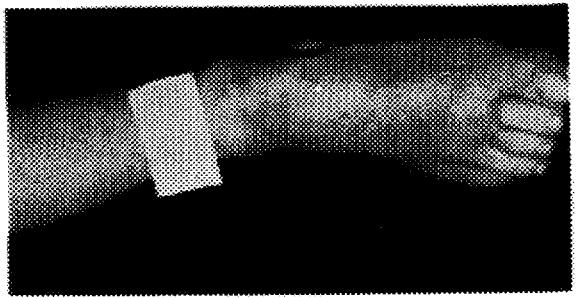
Figure 5A:
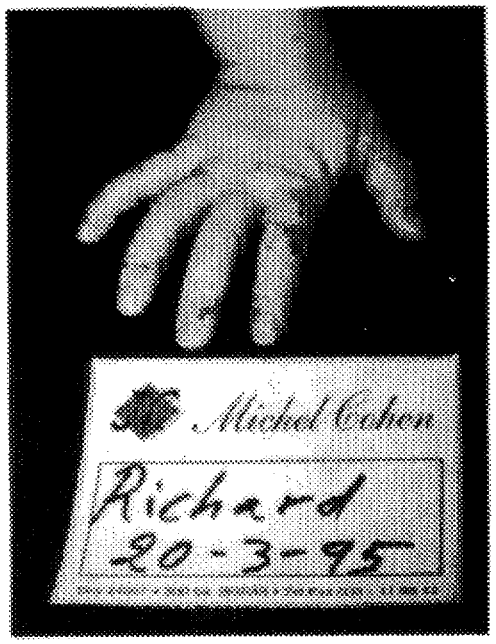
Figure 5B:
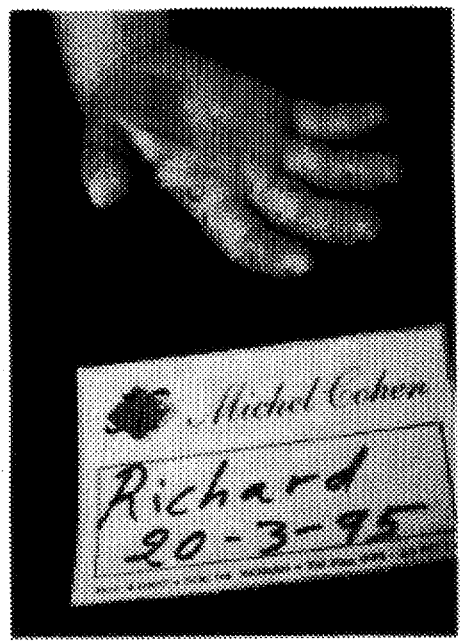
Figure 5C:
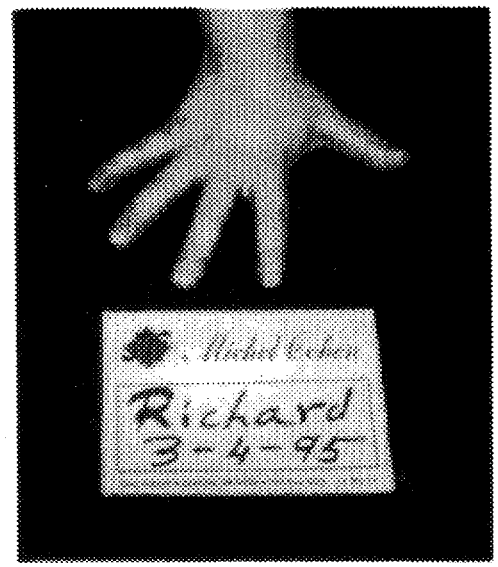
Figure 5D:
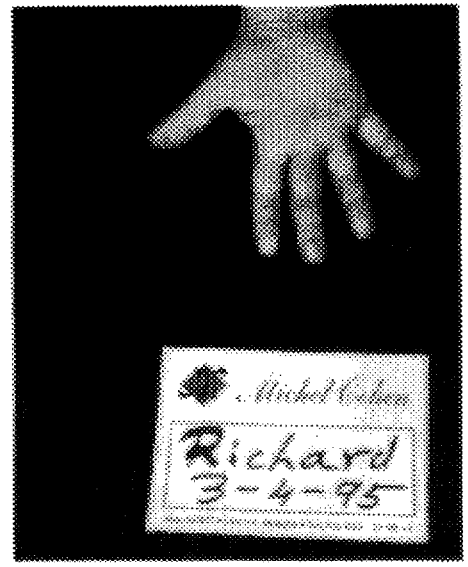
Figure 6A:
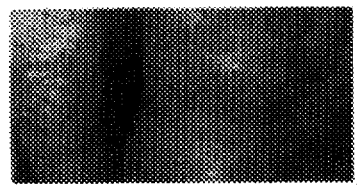
Figure 6B:
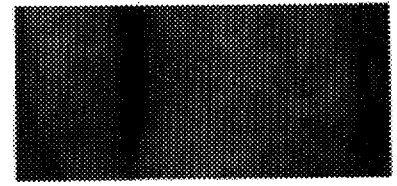
Figure 6C:
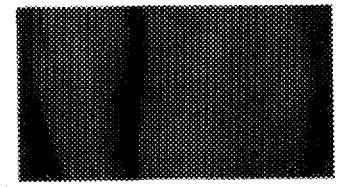
Figure 6D:
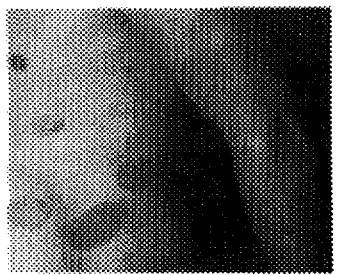
Figure 6E:
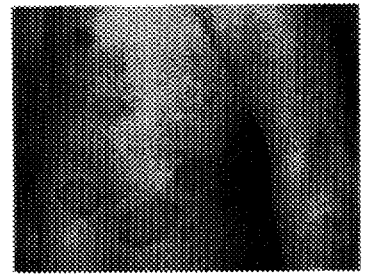
Figure 6F:
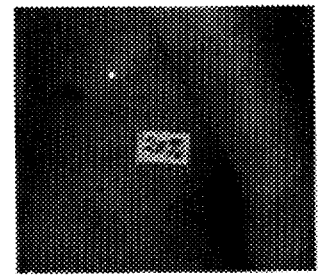
Figure 7A:
Figure 7B:
Figure 7C:
Figure 7D:
Figure 7E:
Figure 7F:
Figure 7G:
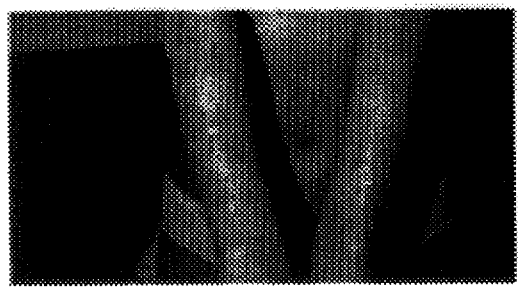
Figure 7H:
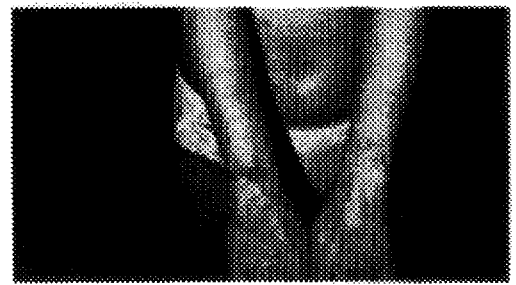
Figure 7I:
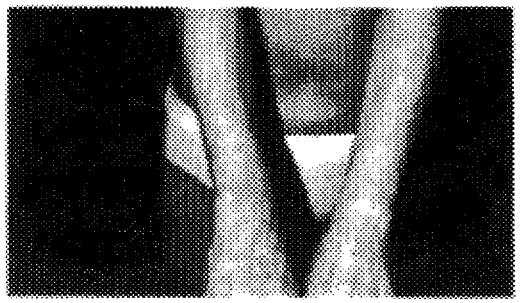
Figure 7J:
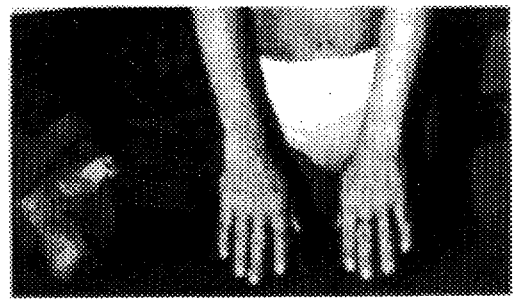

It has now been surprisingly discovered that a combination of said compounds exhibits a synergistic effect which not only heals psoriasis but also cures said condition, so that even after treatment is completed, the psoriasis does not return.

The present invention provides a pharmaceutical composition comprising a synergistic combination of about 0.01–0.15% by wt. triamcinolone acetonide and about 0.04–0.3% by wt. halcinonide as active ingredients therein, in combination with a pharmaceutically acceptable carrier.

Preferably, according to the present invention, there is provided a pharmaceutical composition for treating psoriasis, comprising a synergistic combination of about 0.05–0.15% by wt. triamcinolone acetonide and about 0.2–0.3% by wt. halcinonide as active ingredients therein, in combination with a pharmaceutically acceptable carrier.

Said composition preferably comprises a pharmaceutical composition comprising about 0.1% triamcinolone acetonide and about 0.2% halcinonide. The pharmaceutically acceptable carrier can be any of those known and taught in the prior art.

The formulation of this invention may also contain additives to improve the physical form and the release characteristics. Additives which may be used include diluents, thickness agents, preservatives and penetration enhancers.

The penetration enhancers suitable for the purpose of the invention are the therapeutically acceptable penetration enhancers that do not adversely affect the drug, the skin or the materials for using the ointment.

Examples of penetration enhancers include 1-dodecyl-azacycloheptan-2-one, propylene glycol, surfactants and others.

Thus it will be understood that the present invention also provides a pharmaceutical composition for treating psoriasis comprising a synergistic combination of about 0.01–0.15% by wt. triamcinolone acetonide and about 0.04–0.3% by wt. halcinonide as active ingredient therein when said active ingredients are used in combination with a penetration enhancer.

A preferred formulation comprises a base of about 70% vaselin albun, 10% lanoline and 20% lanet wax and 325 ml water to form about 1 kilogram of ointment cream carrier for said active ingredients.

While the invention will now be described in connection with certain preferred embodiments in the following examples so that aspects thereof may be more fully understood and appreciated, it is not intended to limit the invention to these particular embodiments, On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Two compositions according to the present invention were prepared in the following manner:
Preparation of the Base Vaseline (70%) was mixed with lanolin (20%) and lanet wax (10%) was added while heating at a temperature not exceeding 70° C. and mixing constantly in order to maximize the homogenicity of the base. 30% water was added at 70° C.

Active Ingredients

1a) Per 100 g ointment—200 mg haleinonide
100 mg triamcinolene

1b) Forte, per 100 g ointment—300 mg haleinonide
100 mg triamcinolone

The above amounts of active ingredients were respectively mixed together with a mortar and pestle with the help of a drop of parafin. While mixing constantly the base was added drop by drop at first, then more rapidly, until a total amount of 100 gm was obtained.

COMPARATIVE EXAMPLE 2 a) A comparative composition was prepared as in example 1, however having only 0.1% halcinonide and 0.1% triamcinolone actamide in the final composition.

b) A comparative composition was prepared as in Example 1, having 0.3% halcinonide.

c) A comparative composition was prepared as in Example 1 having 0.3% triamcinolone acetonide.

A volunteer patient having severe psoriasis over the entire body was treated at different sites with compositions 1a, 1b and comparative compositions 2a, 2b and 2c.

The observed results were as follows:

Composition 2a—Some spots of the psoriasis disappeared, but not all, and where they did fade, pink color remained.

Composition 2b—No results—no improvement.

Composition 2c—No results—no improvement.

Composition 1a—Within one week of treatment the psoriasis on the entire area of treatment disappeared with skin returning to normal color except for a few isolated spots of original long established psoriasis. (These spots also disappeared upon treatment with composition 1b).

Composition 1b—Within one week of treatment the spots completely disappeared with skin returning to normal color and with no sign of previous psoriasis.

It should be noted that this experiment was performed on a subject with a serious case of psoriasis covering parts of the entire body and that while the prior art formulations in their maximum permitted dose had no appreciable effect, the compositions of the present invention effected a complete cure.

EXAMPLE 3

Several volunteer patients suffering from psoriasis were treated with composition 1a as prepared in Example 1. The treatment was as follows:

Composition is applied twice a day for two weeks, morning and evening. A very small amount is used each time, massaged very well into the skin. If the psoriasis disappeared by the end of these two weeks, the patient continued use once a day for three weeks. If psoriasis did not completely disappear patient was given composition 1b and treatment given two times a day for two weeks and then once per day for three weeks.

The following results were observed:

Total success of the above treatments was achieved in 70% of the cases in which the psoriasis disappeared completely and did not return for the two year observation period. In the remaining 30%, there was marked improvement but when treatment was stopped, the psoriasis returned.

It is to be noted that on the one hand a combination of 0.1% halcinonide and 0.1% triamcinolone acetonide is insufficient to effect a cure of psoriasis, and on the other hand, combined amounts of active ingredients above 0.4% are inadvisable because they repress adrenaline. Combinations within that range, however, provided that the amount of halcinonide is greater than the amount of triamcinolone acetonide, are effective and contemplated for use according to the present invention.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the fore-going description, and all changes which come within the meaning and range of equivalency of the claims are therefore intended to be embraced therein.

What is claimed is:

1. A pharmaceutical composition comprising triamcinolone acetonide and halcinonide in synergistic and effective amounts in combination with a pharmaceutically acceptable carrier.

2. A pharmaceutical composition comprising about 0.1% triamcinolone acetonide and about 0.1% halcinonide in combination with a pharmaceutical carrier.

3. A pharmaceutical composition according to claim 1, wherein said pharmaceutically acceptable carrier is a topical cream.

4. A pharmaceutical composition comprising triamcinolone acetonide and halcinonide in synergistic and effective amounts in combination with one or more of petroleum jelly, lanoline, and lanet wax.

5. A pharmaceutical composition of claim 4, further comprising water.

6. A pharmaceutical composition comprising about 0.1% triamcinolone acetonide, about 0.1% halcinonide, about 45 to 50% vaseline, about 6.5 to 7.5% lanoline, about 12 to 15% lanet wax, and a remainder of water, wherein, the percent values are characterized by weight.

7. A method for treating psoriasis in a patient comprising topically administering a composition of claim 1.

8. A method for treating psoriasis in a patient comprising topically administering a composition of claim 4.

9. A method for treating psoriasis in a patient comprising topically administering a composition of claim 6.

10. A method for treating dermatitis in a patient comprising topically administering a composition of claim 1.

11. A method for treating dermatitis in a patient comprising topically administering a composition of claim 4.

12. A method for treating dermatitis in a patient comprising topically administering a composition of claim 6.

13. A method for treating eczema in a patient comprising topically administering a composition of claim 1.

14. A method for treating eczema in a patient comprising topically administering a composition of claim 4.

15. A method for treating eczema in a patient comprising topically administering a composition of claim 6.

* * * * *